(12) United States Patent
Kawae et al.

(10) Patent No.: US 6,595,924 B2
(45) Date of Patent: Jul. 22, 2003

(54) CONTROL PANEL FOR ULTRASONIC DIAGNOSTIC APPARATUS HAVING A DEVICE FOR PREVENTING ERRONEOUS OPERATION

(75) Inventors: Sotaro Kawae, Tokyo (JP); Mitsuhiro Nozaki, Tokyo (JP); Masami Uchibori, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/036,608

(22) Filed: Dec. 31, 2001

(65) Prior Publication Data

US 2002/0123684 A1 Sep. 5, 2002

(30) Foreign Application Priority Data

Mar. 5, 2001 (JP) ......................................... 2001-059740

(51) Int. Cl.[7] .................................................. A61B 8/00
(52) U.S. Cl. ...................................................... 600/437
(58) Field of Search ................................. 600/407, 437, 600/438, 439, 440–471; 73/625, 626; 128/916; 367/7, 11, 130, 138; 606/167, 169; 700/1, 2, 20, 78, 83, 84–89; 702/183; 345/700; 334/47

(56) References Cited

U.S. PATENT DOCUMENTS

| | | | | |
|---|---|---|---|---|
| 6,063,030 A | * | 5/2000 | Vara et al. | 600/437 |
| 6,142,940 A | * | 11/2000 | Lathbury et al. | 600/437 |
| 6,210,327 B1 | * | 4/2001 | Brackett et al. | 600/437 |
| 6,210,329 B1 | * | 4/2001 | Christmas et al. | 600/437 |
| 6,306,089 B1 | * | 10/2001 | Coleman et al. | 600/437 |
| 6,361,497 B1 | * | 3/2002 | Lathbury et al. | 600/437 |
| 6,436,040 B1 | * | 8/2002 | Collamore et al. | 600/437 |

* cited by examiner

Primary Examiner—Ali M. Imam
(74) Attorney, Agent, or Firm—Moonray Kojima

(57) ABSTRACT

In order to prevent a troublesome result if a wrong operation button is pressed by mistake, a signal is transmitted from a "New Patient" button 6a to a control section 7' when a normal/lock switching switch 6b' is in a normal mode. When the normal/lock switching switch 6b' is in a lock mode, no signal is transmitted from the "New Patient" button 6a to the control section 7', and an LED 8 is lit.

19 Claims, 5 Drawing Sheets

CONTROL PANEL FOR ULTRASONIC DIAGNOSTIC APPARATUS HAVING A DEVICE FOR PREVENTING ERRONEOUS OPERATION

BACKGROUND OF THE INVENTION

The present invention relates to an ultrasonic diagnostic apparatus, and more particularly to an ultrasonic diagnostic apparatus that can prevent a troublesome result if a wrong operation button is pressed by mistake.

RELATED ART

One conventional ultrasonic diagnostic apparatus comprises a "New Patient" button on its console.

By pressing the "New Patient" button, previous patient information can be reset and the function mode can be switched to one for inputting new patient information, by a fingertip operation.

Moreover, one conventional ultrasonic diagnostic apparatus can function as a personal computer, in addition to functioning as an ultrasonic diagnostic apparatus. For the function as a personal computer, the apparatus comprises a keyboard similar to that provided in a personal computer.

In such an ultrasonic diagnostic apparatus, a personal computer function can be activated during diagnosis of a patient to create a comment using personal computer software.

Recently, the size of ultrasonic diagnostic apparatuses is being reduced, and the space separating operation buttons on the console tends to be reduced.

However, as the space separating the operation buttons becomes smaller, a wrong operation button adjacent to the button that should be pressed is more often pressed by mistake. For example, if the "New Patient" button is pressed by mistake, trouble, such as undesired resetting of the previous patient information, may occur.

Moreover, an operation button for the ultrasonic diagnostic apparatus may be pressed by mistake during keyboard manipulation when the apparatus is functioning as a personal computer. Also in this case, trouble may occur.

SUMMARY OF THE INVENTION

It is therefore an object of the present invention is to provide an ultrasonic diagnostic apparatus that can prevent a troublesome result if a wrong operation button is pressed by mistake.

According to its first aspect, the present invention provides an ultrasonic diagnostic apparatus comprising normal/lock switching means for switching between a normal mode in which operation of at least one predefined operation button is enabled and a lock mode in which operation of the operation button is disabled.

In the ultrasonic diagnostic apparatus of the first aspect, when the lock mode is selected by the normal/lock switching means, a troublesome result can be prevented even if an operation button is pressed by mistake because its operation is disabled.

According to its second aspect, the present invention provides the ultrasonic diagnostic apparatus of the aforementioned configuration, wherein the operation of the operation button is disabled in the lock mode by software.

In the ultrasonic diagnostic apparatus of the second aspect, since the operation of the operation button is disabled by software processing, no hardware change is needed and implementation is easy.

According to its third aspect, the present invention provides the ultrasonic diagnostic apparatus of the aforementioned configuration, wherein the operation of the operation button is disabled in the lock mode by hardware.

In the ultrasonic diagnostic apparatus of the third aspect, since the operation of the operation button is disabled by hardware, no software processing change is needed and implementation is easy.

According to its fourth aspect, the present invention provides the ultrasonic diagnostic apparatus of the aforementioned configuration, wherein the at least one operation button includes an operation button for resetting patient information in effect before the operation button is operated and switching to a function for inputting new patient information.

In the ultrasonic diagnostic apparatus of the fourth aspect, current patient information is prevented from being reset by mistake even if the "New Patient" button is pressed by mistake because the operation of the "New patient" button is disabled.

According to its fifth aspect, the present invention provides the ultrasonic diagnostic apparatus of the aforementioned configuration, wherein a shift from a function for a previous patient to a function for a new patient is disabled in the lock mode.

In the ultrasonic diagnostic apparatus of the fifth aspect, current patient information is prevented from being reset by mistake.

According to its sixth aspect, the present invention provides the ultrasonic diagnostic apparatus of the aforementioned configuration, wherein a scan function is suspended in the lock mode.

In the ultrasonic diagnostic apparatus of the sixth aspect, since scan data is not updated, the scan data at the time of starting the lock mode can be kept.

According to its seventh aspect, the present invention provides the ultrasonic diagnostic apparatus of the aforementioned configuration, wherein operation for inputting a comment and an operation for data analysis are enabled in the lock mode.

In the ultrasonic diagnostic apparatus of the seventh aspect, since the apparatus can remain in the lock mode when a comment is input and data analysis is performed, there is no need for concern that pressing an operation button will cause a troublesome result.

According to its eighth aspect, the present invention provides the ultrasonic diagnostic apparatus of the aforementioned configuration, wherein a function as a personal computer is enabled in the lock mode.

In the ultrasonic diagnostic apparatus of the eighth aspect, since the apparatus can remain in the lock mode when the apparatus is functioning as a personal computer, there is no need for concern that pressing an operation button will cause a troublesome result.

According to its ninth aspect, the present invention provides the ultrasonic diagnostic apparatus of the aforementioned configuration, wherein the normal/lock switching means comprises a push button and press detecting means for detecting a press of the push button for not less than T ($\geq 2$) seconds, and is enabled by an operation of pressing the push button for not less than T seconds.

In the ultrasonic diagnostic apparatus of the ninth aspect, since the switching between the normal and lock modes is enabled only after the push button has been pressed for not less than two seconds, erroneous switching between the normal and lock modes can be prevented. (The time that a push button is pressed by mistake is generally no more than one second.)

According to its tenth aspect, the present invention provides the ultrasonic diagnostic apparatus of the aforementioned configuration, wherein the enablement of the normal/lock switching means requires an operation of two steps or more.

In the ultrasonic diagnostic apparatus of the tenth aspect, since the switching between the normal and lock modes is enabled only when an operation of two steps or more is performed, erroneous switching between the normal and lock modes can be prevented. (An operation of two steps or more is unlikely to be performed by mistake.)

According to its eleventh aspect, the present invention provides the ultrasonic diagnostic apparatus of the aforementioned configuration, wherein the normal/lock switching means comprises a push button, a cover over the push button, and press detecting means for detecting a press of the push button, and is enabled by a first-step operation of opening the cover and a second-step operation of pressing the push button.

In the ultrasonic diagnostic apparatus of the eleventh aspect, since the switching between the normal and lock modes is enabled only when a two-step operation involving opening a cover and pressing a push button is performed, erroneous switching between the normal and lock modes can be prevented. (A two-step operation involving opening a cover and pressing a push button is unlikely to be performed by mistake.)

According to its twelfth aspect, the present invention provides the ultrasonic diagnostic apparatus of the aforementioned configuration, wherein the normal/lock switching means comprises simultaneous operation detecting means for detecting a simultaneous operation of a plurality of predefined keys, and is enabled by simultaneously operating the plurality of keys.

In the ultrasonic diagnostic apparatus of the twelfth aspect, since the switching between the normal and lock modes is enabled only when a plurality of predefined keys are simultaneously operated, erroneous switching between the normal and lock modes can be prevented. (A combination of keys that are unlikely to be simultaneously pressed may be selected as the predefined keys.)

According to its thirteenth aspect, the present invention provides the ultrasonic diagnostic apparatus of the aforementioned configuration, wherein notice of the lock mode being in effect is displayed on a screen.

In the ultrasonic diagnostic apparatus of the thirteenth aspect, the fact that the lock mode is in effect can be known from the screen display.

According to its fourteenth aspect, the present invention provides the ultrasonic diagnostic apparatus of the aforementioned configuration, wherein notice of the lock mode being in effect is shown by light emitting means.

In the ultrasonic diagnostic apparatus of the fourteenth aspect, the fact that the lock mode is in effect can be known from the on/off condition of a lamp or LED.

According to its fifteenth aspect, the present invention provides the ultrasonic diagnostic apparatus of the aforementioned configuration, further comprising a keyboard whose keys are arranged within an area no wider than 400 mm.

In the ultrasonic diagnostic apparatus of the fifteenth aspect, a troublesome result caused by pressing a wrong key can be prevented even though a small keyboard is employed in which the probability of pressing a wrong operation button is high.

According to its sixteenth aspect, the present invention provides the ultrasonic diagnostic apparatus of the aforementioned configuration, wherein the ultrasonic diagnostic apparatus is started up in the normal mode when the power is turned on.

In the ultrasonic diagnostic apparatus of the sixteenth aspect, since the apparatus is always started up in the normal mode when the power is turned on, ease of use is improved. For example, if regular operation becomes impossible when the apparatus is being operated as a personal computer and the normal mode cannot be recovered, the apparatus can be operated as an ultrasonic diagnostic apparatus by turning the power on again.

According to the ultrasonic diagnostic apparatus of the present invention, a troublesome result can be prevented if a wrong operation button is pressed by mistake.

Further objects and advantages of the present invention will be apparent from the following description of the preferred embodiments of the invention as illustrated in the accompanying drawings.

DETAILED DESCRIPTION OF THE INVENTION

The present invention will now be described in detail with reference to embodiments shown in the accompanying drawings. It should be noted that the present invention is not limited to these embodiments.

First Embodiment

Figure 1:
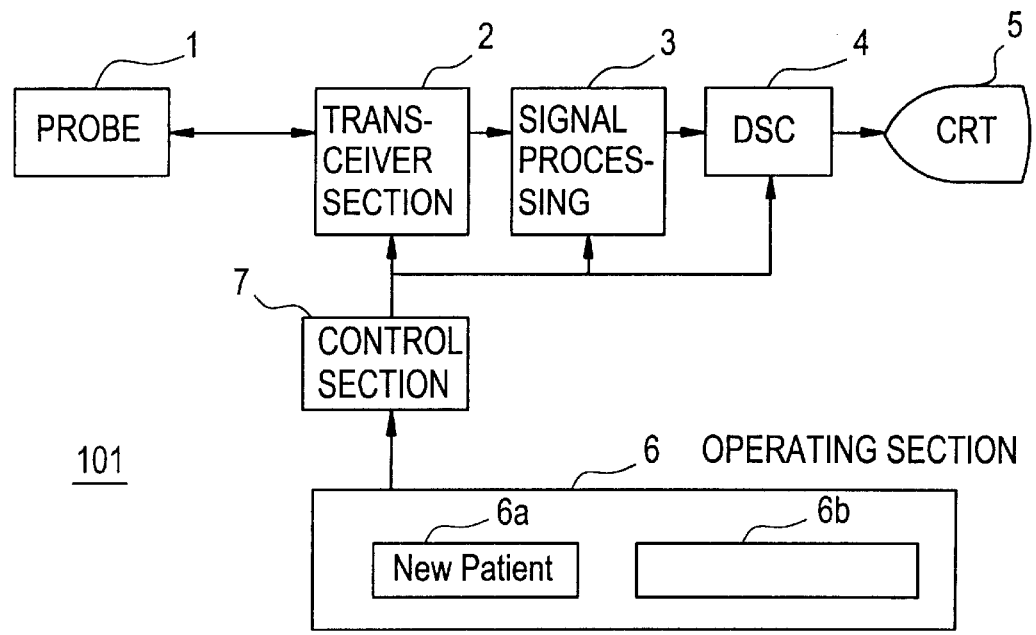
FIG. 1 is a block diagram showing an ultrasonic diagnostic apparatus in accordance with a first embodiment.

FIG. 1 is a block diagram showing an ultrasonic diagnostic apparatus 101 in accordance with a first embodiment of the present invention.

The ultrasonic diagnostic apparatus 101 comprises: a probe 1 for transmitting ultrasonic pulses into a subject and receiving ultrasonic echoes from the subject; a transceiver section 2 for changing the acoustic line direction to scan the interior of the subject and generating an acoustic line signal in each acoustic line direction; a signal processing section 3 for generating B-mode image data and CFM (color flow mapping) image data based on the intensity and the Doppler component of the acoustic line signals; a display control section 4 for controlling display of images and messages etc.; a display 5 for displaying the images and messages; an operating section 6 for a human operator to perform operations; and a control section 7 for controlling the overall function.

The operating section 6 includes a "New Patient" button 6a for resetting previous patient information and switching to the function for inputting new patient information, and a normal/lock switching button 6b for switching between a normal mode in which operation of the "New Patient" button 6a is enabled and a lock mode in which operation of the "New Patient" button 6a is disabled.

Figure 2:
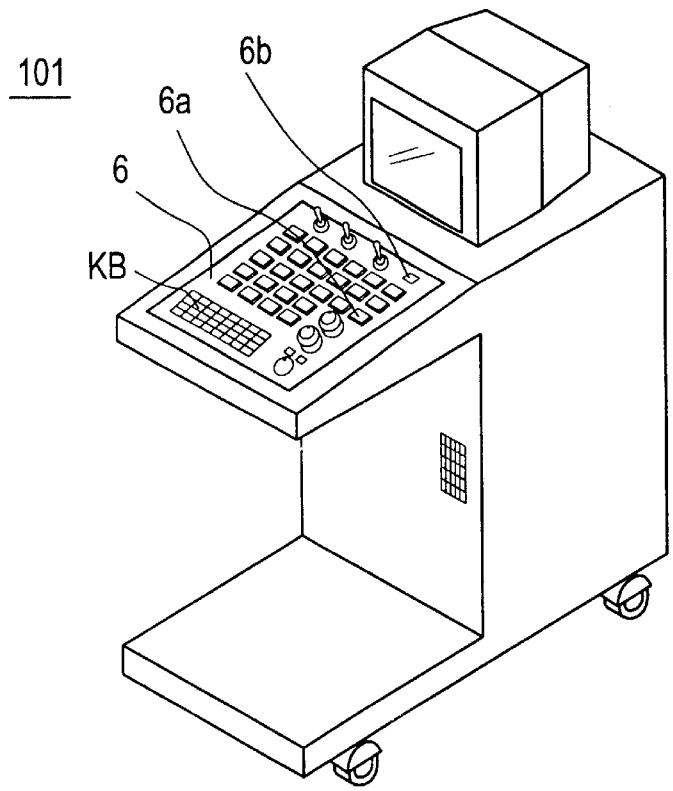
FIG. 2 is a perspective view showing the ultrasonic diagnostic apparatus in accordance with the first embodiment.

FIG. 2 is a perspective view of the ultrasonic diagnostic apparatus 101 (in which the probe is omitted).

The "New Patient" button 6a, the normal/lock switching button 6b, and a keyboard KB etc. are provided in an operating panel of the operating section 6.

The ultrasonic diagnostic apparatus 101 can also function as a personal computer, and the computer can be operated by using the keyboard KB.

The keys of the keyboard KB are arranged within an area no wider than 400 mm for size reduction.

Figure 3:
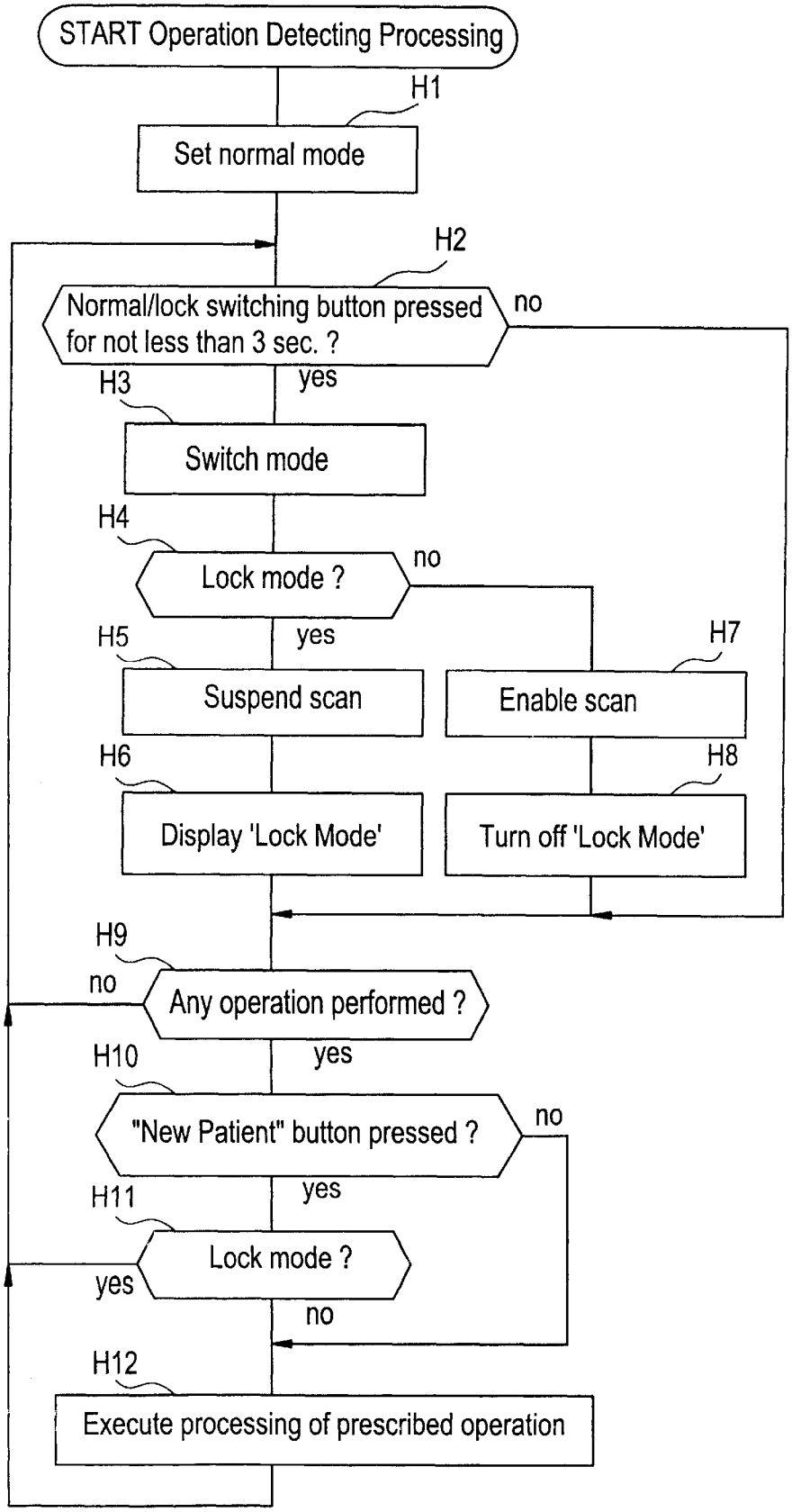
FIG. 3 is a flow chart showing operation detecting processing by the ultrasonic diagnostic apparatus in accordance with the first embodiment.

FIG. 3 is a flow chart showing operation detecting processing executed by the control section 7 in the ultrasonic diagnostic apparatus 101. The operation detecting processing is activated when the power is turned on.

In Step H1, the mode is set to the normal mode.

In Step H2, a check is made as to whether the normal/lock switching button 6b has been pressed for not less than three seconds. If the normal/lock switching button 6b has been pressed for not less than three seconds, the process goes to Step H3; otherwise to Step H9.

In Step H3, if the current mode is the normal mode, the mode is changed to the lock mode; and if the current mode is the lock mode, the mode is changed to the normal mode.

In Step H4, if the mode has been changed to the lock mode, the process goes to H5; and if the mode has been changed to the normal mode, the process goes to H7.

In Step H5, a scan function is suspended.

In Step H6, a message or symbol indicating that the lock mode is in effect is displayed on a screen of the display 5.

Then, the process goes to Step H9.

In Step H7, the scan function is enabled.

In Step H8, the message or symbol displayed on the screen of the display 5 to indicate that the lock mode is in effect is turned off.

Then, the process goes to Step H9.

In Step H9, a check is made as to whether any operation has been performed. If some operation has been performed, the process goes to Step H10; otherwise goes back to Step H2.

In Step H10, if the "New Patient" button 6a was pressed, the process goes to Step H11; otherwise goes to Step H12.

In Step H11, the process goes back to Step H2 if the apparatus is in the lock mode, and goes to Step H12 if the apparatus is in the normal mode.

In Step H12, processing prescribed by the operation is executed.

Then, the process goes back to Step H2.

According to the ultrasonic diagnostic apparatus 101, the following effects can be obtained:

(1) Even if the "New Patient" button 6a is pressed by mistake, the current patient information is prevented from being reset by mistake because the operation of the "New Patient" button 6a is disabled when the lock mode is selected by the normal/lock switching button 6b;

(2) Since the operation of the "New Patient" button 6a is disabled by software processing, no hardware change is needed and implementation is easy;

(3) Since scan data is not updated in the lock mode, the scan data at the time of starting the lock mode can be kept;

(4) Input of a comment and data analysis can be performed even in the lock mode. Even if the "New Patient" button 6a is pressed by mistake during that time, a troublesome result can be prevented because the operation of the "New Patient" button 6a is disabled;

(5) The apparatus can function as a personal computer even in the lock mode. Even if the "New Patient" button 6a is pressed by mistake during that time, a troublesome result can be prevented because the operation of the "New Patient" button 6a is disabled;

(6) Since the switching between the normal and lock modes is enabled only after the push button has been pressed for not less than three seconds, erroneous switching between the normal and lock modes can be prevented;

(7) The fact that the lock mode is in effect can be known from the screen display;

(8) Even when a small keyboard is employed in which the probability of pressing a wrong operation button is high, a troublesome result caused by pressing a wrong key can be prevented; and (9) Since the apparatus is always started up in the normal mode when the power is turned on, ease of use is improved. For example, if regular operation becomes impossible when the apparatus is being operated as a personal computer and the normal mode cannot be recovered, the apparatus can be operated as an ultrasonic diagnostic apparatus by turning the power on again.

While the preceding description was made regarding a case in which the operation of the "New Patient" button 6a is disabled in the lock mode, it is also possible to disable other operations.

Second Embodiment

Figure 4:
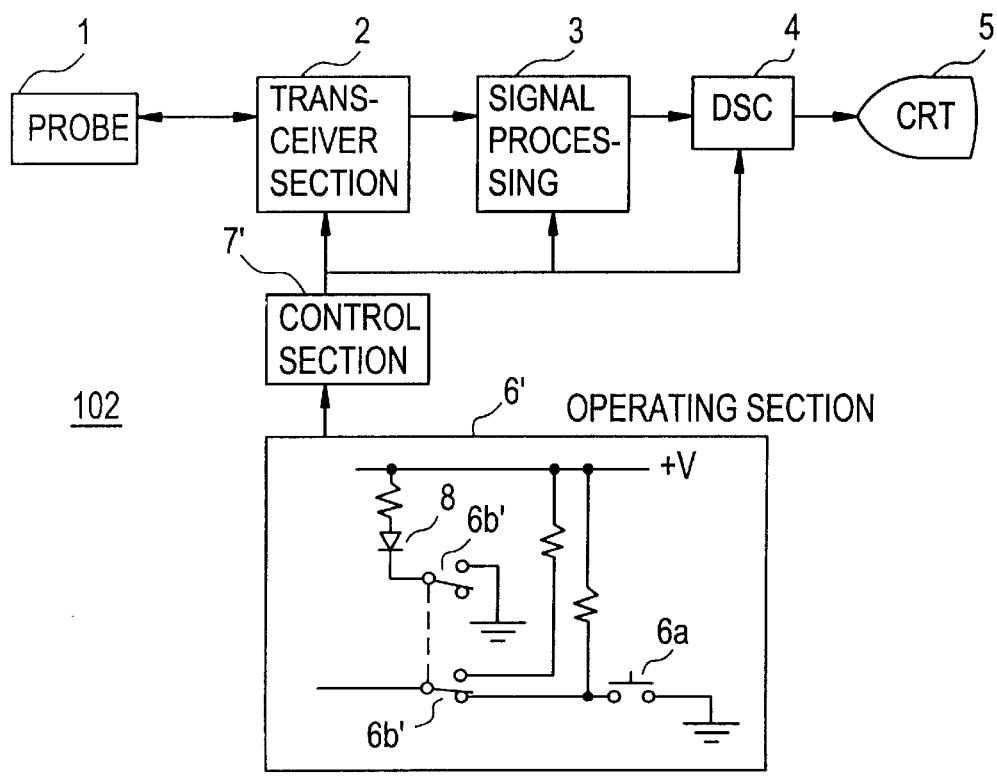
FIG. 4 is a block diagram showing an ultrasonic diagnostic apparatus in accordance with a second embodiment.

FIG. 4 is a block diagram showing an ultrasonic diagnostic apparatus 102 in accordance with a second embodiment of the present invention.

The ultrasonic diagnostic apparatus 102 comprises: a probe 1 for transmitting ultrasonic pulses into a subject and receiving ultrasonic echoes from the subject; a transceiver section 2 for changing the acoustic line direction to scan the interior of the subject and generating an acoustic line signal in each acoustic line direction; a signal processing section 3 for generating B-mode image data and CFM image data based on the intensity and the Doppler component of the acoustic line signals; a display control section 4 for controlling display of images and messages etc.; a display 5 for displaying the images and messages; an operating section 6' for a human operator to perform operations; and a control section 7' for controlling the overall function.

The operating section 6' includes a "New Patient" button 6a for resetting previous patient information and switching to the function for inputting new patient information, and a normal/lock switching switch 6b' for switching between a normal mode in which operation of the "New Patient" button 6a is enabled and a lock mode in which operation of the "New Patient" button 6a is disabled.

When the normal/lock switching switch 6b' is in the normal mode, a signal is transmitted from the "New Patient" button 6a to the control section 7'. When the normal/lock switching switch 6b' is in the lock mode, no signal is transmitted from the "New Patient" button 6a to the control section 7', and an LED 8 is lit.

Figure 5:
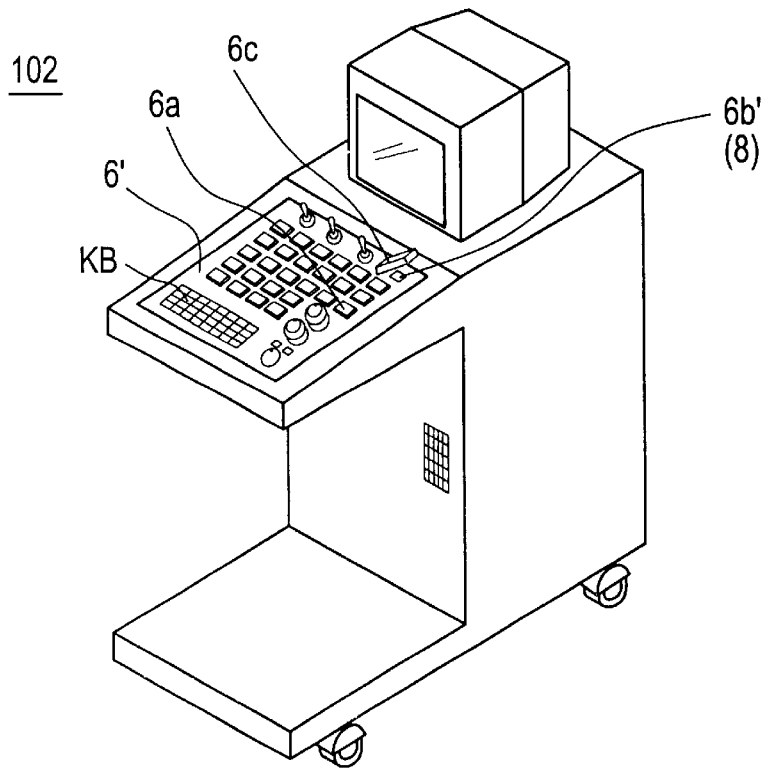
FIG. 5 is a perspective view showing the ultrasonic diagnostic apparatus in accordance with the second embodiment.

FIG. 5 is a perspective view of the ultrasonic diagnostic apparatus 102 (in which the probe is omitted).

The "New Patient" button 6a, the normal/lock switching switch 6b', and a keyboard KB etc. are provided in an operating panel of the operating section 6'.

The normal/lock switching switch 6b' is protected by a cover 6c. Moreover, the LED 8 is incorporated in the normal/lock switching switch 6b'.

The ultrasonic diagnostic apparatus 102 can also function as a personal computer, and the computer can be operated by using the keyboard KB.

The keys on the keyboard KB are arranged within an area no wider than 400 mm for size reduction.

When the normal/lock switching switch 6b' is to be operated, an operation of opening the cover 6c and an operation of pressing the normal/lock switching switch 6b' are needed; i.e., a two-step operation is needed.

According to the ultrasonic diagnostic apparatus 102, the following effects can be obtained:

(1) Even if the "New Patient" button 6a is pressed by mistake, the current patient information is prevented from being reset by mistake because the operation of the "New Patient" button 6a is disabled (no signal is transmitted to the control section 7') when the lock mode is selected by the normal/lock switching button 6b';

(2) Since the operation of the "New Patient" button 6a is disabled by hardware, no software change is needed and implementation is easy;

(3) Input of a comment and data analysis can be performed even in the lock mode. Even if the "New Patient" button 6a is pressed by mistake during that time, a troublesome result can be prevented because the operation of the "New Patient" button 6a is disabled;

(4) The apparatus can function as a personal computer even in the lock mode. Even if the "New Patient" button 6a is pressed by mistake during that time, a troublesome result can be prevented because the operation of the "New Patient" button 6a is disabled;

(5) Since the switching between the normal and lock modes is enabled only when an operation of two steps or more is performed, erroneous switching between the normal and lock modes can be prevented;

(6) The fact that the lock mode is in effect can be known from the light of the LED 8; and (7) Even when a small keyboard is employed in which the probability of pressing a wrong operation button is high, a troublesome result caused by pressing a wrong key can be prevented.

While the preceding description was made regarding a case in which the operation of the "New Patient" button 6a is disabled in the lock mode, it is also possible to disable other operations.

Third Embodiment

Figure 6:
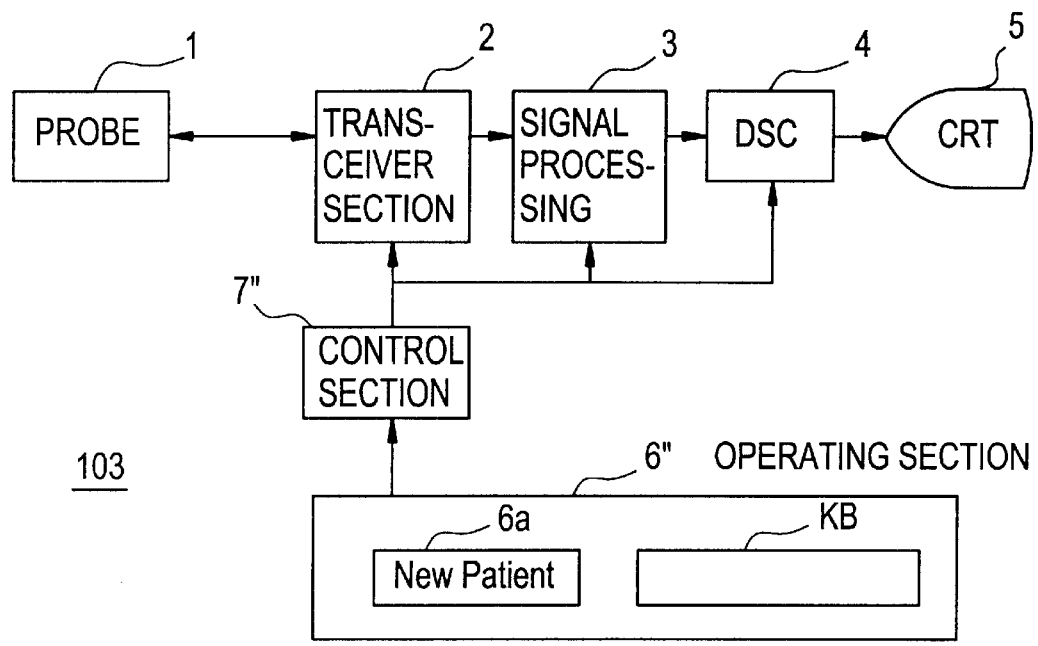
FIG. 6 is a block diagram showing an ultrasonic diagnostic apparatus in accordance with a third embodiment.

FIG. 6 is a block diagram showing an ultrasonic diagnostic apparatus 103 in accordance with a third embodiment of the present invention.

The ultrasonic diagnostic apparatus 103 comprises: a probe 1 for transmitting ultrasonic pulses into a subject and receiving ultrasonic echoes from the subject; a transceiver section 2 for changing the acoustic line direction to scan the interior of the subject and generating an acoustic line signal in each acoustic line direction; a signal processing section 3 for generating B-mode image data and, CFM image data based on the intensity and the Doppler component of the acoustic line signals; a display control section 4 for controlling display of images and messages etc.; a display 5 for displaying the images and messages; an operating section 6" for a human operator to perform operations; and a control section 7" for controlling the overall function.

The operating section 6" includes a "New Patient" button 6a for resetting previous patient information and switching to the function for inputting new patient information, and a keyboard KB.

The keyboard KB can be used to switch between a normal mode in which operation of the "New Patient" button 6a is enabled and a lock mode in which operation of the a "New Patient" button 6a is disabled.

Figure 7:
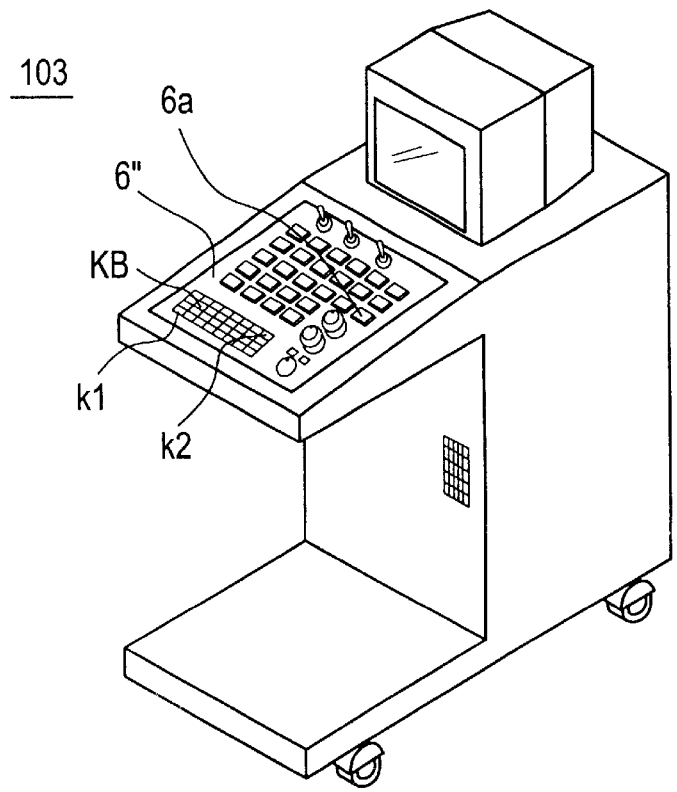
FIG. 7 is a perspective view showing the ultrasonic diagnostic apparatus in accordance with the third embodiment.

FIG. 7 is a perspective view of the ultrasonic diagnostic apparatus 103 (in which the probe is omitted).

The "New Patient" button 6a and a keyboard KB etc. are provided in an operating panel of the operating section 6"

The normal and lock modes can be switched by simultaneously pressing keys k1 and k2 spaced apart from each other on the keyboard KB.

The ultrasonic diagnostic apparatus 103 can also function as a personal computer, and the computer can be operated by using the keyboard KB.

The keys on the keyboard KB are arranged within an area no wider than 400 mm for size reduction.

Figure 8:
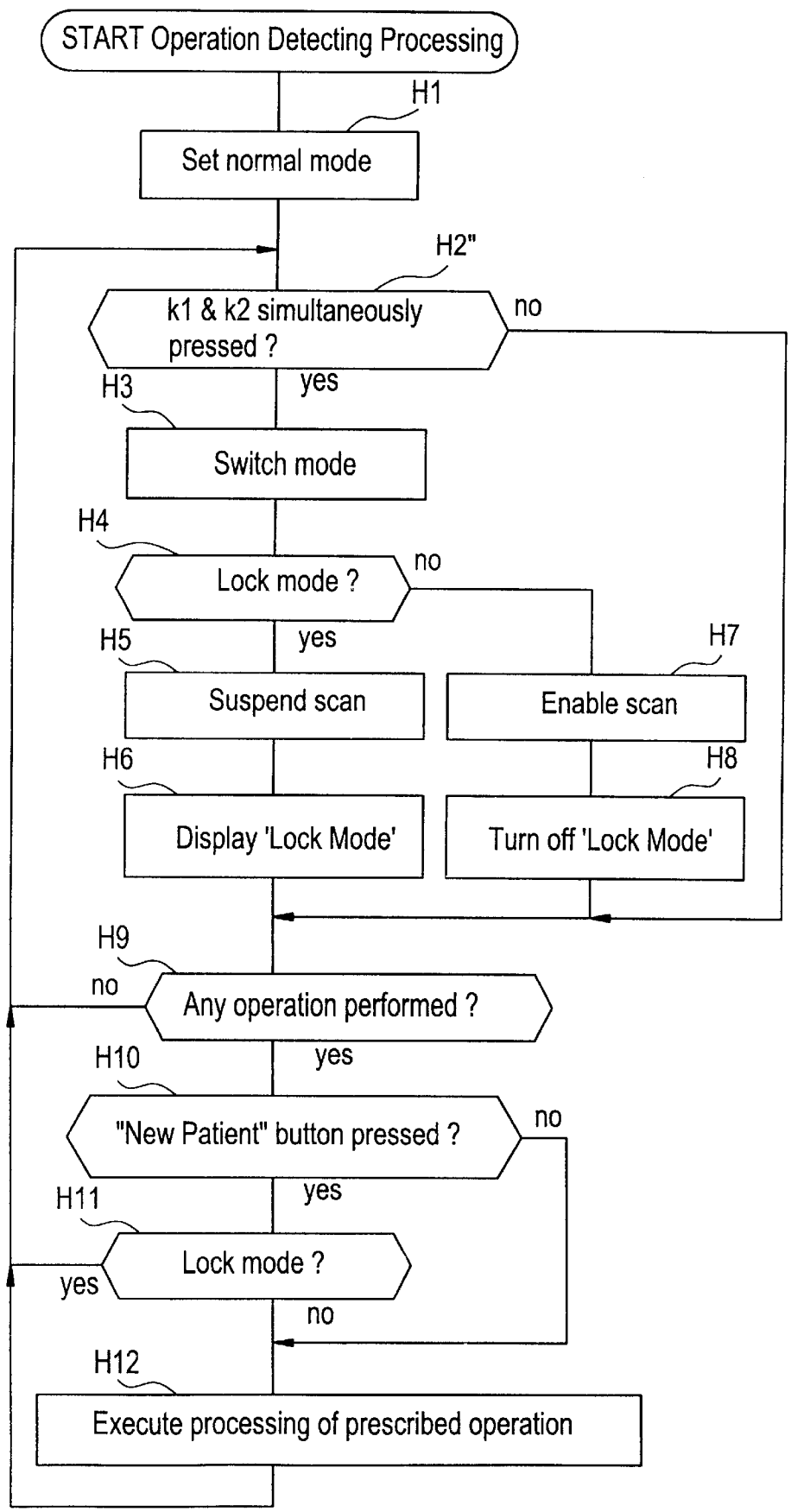
FIG. 8 is a flow chart showing operation detecting processing by the ultrasonic diagnostic apparatus in accordance with the third embodiment.

FIG. 8 is a flow chart showing operation detecting processing executed by the control section 7" in the ultrasonic diagnostic apparatus 103. The operation detecting processing is activated when the power is turned on.

In Step H1, the mode is set to the normal mode.

In Step H2", a check is made as to whether the spaced keys k1 and k2 of the keyboard KB have been simultaneously pressed. If so, the process goes to Step H3; otherwise to Step H9.

In Step H3, if the current mode is the normal mode, the mode is changed to the lock mode; and if the current mode is the lock mode, the mode is changed to the normal mode.

In Step H4, if the mode has been changed to the lock mode, the process goes to H5; and if the mode has been changed to the normal mode, the process goes to H7.

In Step H5, a scan function is suspended.

In Step H6, a message or symbol indicating that the lock mode is in effect is displayed on a screen of the display 5.

Then, the process goes to Step H9.

In Step H7, the scan function is enabled.

In Step H8, the message or symbol displayed on the screen of the display 5 to indicate that the lock mode is in effect is turned off.

Then, the process goes to Step H9.

In Step H9, a check is made as to whether any operation has been performed. If some operation has been performed, the process goes to Step H10; otherwise goes back to Step H2.

In Step H10, if the "New Patient" button 6a was pressed, the process goes to Step H11; otherwise goes to Step H12.

In Step H11, the process goes back to Step H2 if the apparatus is in the lock mode, and goes to Step H12 if the apparatus is in the normal mode.

In Step H12, processing prescribed by the operation is executed.

Then, the process goes back to Step H2.

According to the ultrasonic diagnostic apparatus 103, the following effects can be obtained:

(1) Even if the "New Patient" button 6a is pressed by mistake, the current patient information is prevented from being reset by mistake because the operation of the "New Patient" button 6a is disabled when the lock mode is selected by simultaneously pressing the spaced keys k1 and k2;

(2) Since the operation of the "New Patient" button 6a is disabled by software processing, no hardware change is needed and implementation is easy;

(3) Since scan data is not updated in the lock mode, the scan data at the time of starting the lock mode can be kept;

(4) Input of a comment and data analysis can be performed even in the lock mode. Even if the "New Patient" button 6a is pressed by mistake during that time, a troublesome result can be prevented because the operation of the "New Patient" button 6a is disabled;

(5) The apparatus can function as a personal computer even in the lock mode. Even if the "New Patient" button 6a is pressed by mistake during that time, a troublesome result can be prevented because the operation of the "New Patient" button 6a is disabled;

(6) Since the switching between the normal and lock modes is enabled only when the two keys k1 and k2 spaced apart from each other are simultaneously pressed, erroneous switching between the normal and lock modes can be prevented;

(7) The fact that the lock mode is in effect can be known from the screen display;

(8) Even when a small keyboard is employed in which the probability of pressing a wrong operation button is high, a troublesome result caused by pressing a wrong key can be prevented; and (9) Since the apparatus is always started up in the normal mode when the power is turned on, ease of use is improved. For example, if regular operation becomes impossible when the apparatus is being operated as a personal computer and the normal mode cannot be recovered, the apparatus can be operated as an ultrasonic diagnostic apparatus by turning the power on again.

While the preceding description was made regarding a case in which the operation of the "New Patient" button 6a is disabled in the lock mode, it is also possible to disable other operations.

Many widely different embodiments of the invention may be configured without departing from the spirit and the scope of the present invention. It should be understood that the present invention is not limited to the specific embodiments described in the specification, except as defined in the appended claims.

What is claimed is:

1. A control panel for an ultrasonic diagnostic apparatus, said control panel comprising:

an operation button means, including reset means for resetting previous patient information and new information means for inputting new patient information; and switching means for switching between a first mode in which operation of said operation button means is normally operative and a second mode in which operation caused by said operation button means is disabled, said switching means including a push button means, detecting means for detecting operation of said push button for a period of time not less than a preset time period, and means for causing said operation button means to be disabled when said detector means detects said preset time period.

2. The panel of claim 1, wherein operation caused by said operation button means is disabled by use of software.

3. The panel of claim 1, wherein operation caused by said operation button means is disabled by use of hardware.

4. The panel of claim 1, wherein said operation button means comprises:

shifting means for shifting from a function for a previous patient information to a function for a new patent information, and means for causing said shifting means to be disabled.

5. The panel of claim 1, wherein said switching button means comprises:

means for providing a scan function, and means for suspending said scan function.

6. The panel of claim 1, further comprising:

input means for inputting a comment and an operation for data analysis, and enable means for enabling said input means to be in said second mode.

7. The panel of claim 1, further comprising:

means for inputting a function as a personal computer.

8. The panel of claim 1, wherein said switching means comprises means for operating said switching means in two or more steps.

9. The panel of claim 8, wherein said switching means further comprises:

a manually movable cover for said push button, wherein in an open position said push button is exposed for manual pressing, and in a closed position said push button is covered by said cover so as to protect said push button from accidental pressing.

10. The panel of claim 1, further comprising a plurality of keys; and wherein said switching means comprises:

means for detecting simultaneous operation of said plurality of keys; and means for causing said operation button means to be disabled when said plurality of keys are detected operating simultaneously.

11. The panel of claim 1, further comprising means for displaying existence of said second mode.

12. The panel of claim 1, wherein said means for displaying comprises a light emitting means.

13. The panel of claim 1, further comprising a keyboard including keys arranged in an area no wider than 400 mm.

14. The panel of claim 1, wherein said first mode is caused when power is applied to said panel.

15. A method of protecting against erroneous removal of previous information using a control panel in an ultrasonic diagnostic apparatus, said control panel having an operation button, and a switching means for causing a switch mode wherein said operation button is operable, and a lock mode wherein operation caused by said operation button is disabled, said method comprising the steps of:

(H-1) setting a normal operation mode;

(H-2) determining whether said switching means is pressed for not less than a preset time period;

in the event an answer to step (H-2) is no, the following steps are taken:

(H-9) determining whether any operation is performed, and when an answer to step (H-9) is yes, then (H-10) determining whether said operation button is pressed, and when an answer to step (H-10) is yes, then (H-11) determining whether there is a lock mode, and when an answer to step (H-11) is no, then (H-12) executing processing of a prescribed operation, and in the event an answer to step (H-2) is yes, the following steps are taken:

(H-3) providing a switch mode, then (H-4) determining existence of a lock mode, and when an answer to step (H-4) is yes, then the following steps are taken:

(H-5) suspending scan, then (H-6) displaying a lock mode, and then going to step (H-9), then step (H-10), then step (H-11) and then step (H-12); and when an answer to step (H-4) is no, then the following steps of taken:

(H-7) enabling scanning, then (H-8) turning off the lock mode, and then going to step (H-9), then step (H-10), then step (H-11) and then step (H-12).

16. The method of claim 15, wherein when an answer to step (H-9) is no, then step (H-2) is repeated; and when an answer to step (H-11) is yes, then step (H-2) is repeated.

17. The method of claim 15, wherein said preset time period is equal to or greater than 2 seconds.

18. The method of claim 17, wherein said preset time period is less than 3 seconds.

19. The method of claim 15, wherein said switching means comprises two separate keys which are simultaneously pressed to determine said lock mode.

* * * * *